United States Patent
Meiwes et al.

[11] Patent Number: 5,990,127
[45] Date of Patent: Nov. 23, 1999

[54] PROCESS FOR THE PREPARATION OF 4-(4-(4-(HYDROXYBIPHENYL)-1-PIPERIDINYL)-1-HYDROXYBUTYL)-α,α-DIMETHYLPHENYLACETIC ACID AND PHOSPHORYLATED DERIVATIVES

[75] Inventors: Johannes Meiwes, Idstein; Manfred Worm, Wiesbaden, both of Germany

[73] Assignee: Hoechst Marion Roussel Deutschland GmbH, Frankfurt am Main, Germany

[21] Appl. No.: 09/036,673

[22] Filed: Mar. 9, 1998

[30] Foreign Application Priority Data

Mar. 11, 1997 [DE] Germany .......................... 197 09 898
Nov. 21, 1997 [DE] Germany .......................... 197 51 498

[51] Int. Cl.$^6$ ............................................. C12P 17/12
[52] U.S. Cl. ............................ 514/317; 546/22; 546/239; 546/241
[58] Field of Search ........................... 546/22, 239, 241; 514/317

[56] References Cited

U.S. PATENT DOCUMENTS

| | | |
|---|---|---|
| 4,254,129 | 3/1981 | Carr et al. . |
| 4,285,957 | 8/1981 | Carr et al. . |
| 5,204,249 | 4/1993 | Schwartz et al. . |

FOREIGN PATENT DOCUMENTS

| | | |
|---|---|---|
| 23 03 306 C3 | 8/1973 | Germany . |
| 30 07 498 C2 | 10/1980 | Germany . |
| 40 34 218 A1 | 4/1992 | Germany . |
| WO 92/06992 | 4/1992 | WIPO . |

OTHER PUBLICATIONS

Patent Abstract of Japan, Band 15, No. 60 (C–805), Feb. 13, 1991; & JP 02–288883 A (Sankyo Co Ltd), Nov. 28, 1990.
H. Konzett et al., "Versuchsanordnung zu Untersuchungen an der Bronchialmuskulatur", Arch. Exp. Path. U. Pharmak., 195:71–74 (1940).
S. Schwartz et al., "Microbial Oxidation of Ebastine", Appl. Microbiol Biotechnol., 44:731–735 (1996).

*Primary Examiner*—John Kight
*Assistant Examiner*—Raymond Covington
*Attorney, Agent, or Firm*—Finnegan, Henderson, Farabow, Garrett & Dunner, L.L.P.

[57] ABSTRACT

The invention relates to the preparation of the compound 4-(4-(4-(hydroxydiphenyl)-1-piperidinyl)-1-hydroxybutyl)-α,α-dimethylphenylacetic acid and its phosphorylated derivatives. These compounds can be prepared from α-(p-tert-butylphenyl)-4-(α-hydroxy-α-phenylbenzyl)-1-piperidinylbutanol with the aid of fungi of the genus Cunninghamella or Absidia. The compounds according to the present invention can be used as pharmaceuticals for the treatment of allergic disorders, allergic rhinitis or asthma. Compounds of the formula II

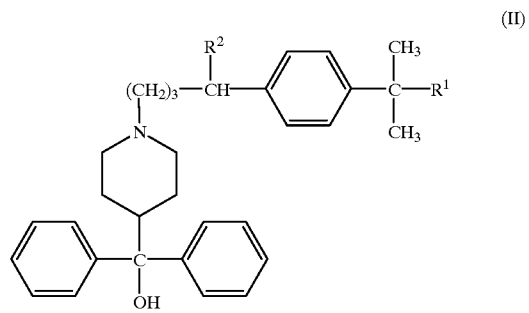

in which $R^1$ is —$CH_2$—O—$P(O)(OH)_2$ and $R^2$ is —OH; $R^1$ is —$CH_3$ and $R^2$ is —O—$P(O)(OH)_2$; or $R^1$ is —COOH and $R^2$ is —O—$P(O)(OH)_2$ are produced by the process according to the present invention and are suitable as pharmaceuticals with antihistamine action.

14 Claims, No Drawings

PROCESS FOR THE PREPARATION OF 4-(4-(4-(HYDROXYBIPHENYL)-1-PIPERIDINYL)-1-HYDROXYBUTYL)-α,α-DIMETHYLPHENYLACETIC ACID AND PHOSPHORYLATED DERIVATIVES

The present invention relates to a microbial process for the preparation of 4-(4-(4-(hydroxydiphenyl)-1-piperidinyl)-1-hydroxybutyl)-α,α-dimethylphenylacetic acid (compound 1) and phosphorylated derivatives of α-(p-tertiary-butylphenyl)-4-(α-hydroxy-α-phenylbenzyl)-1-piperidinylbutanol (compound 2), and their use as pharmaceuticals. The present invention furthermore relates to a microbial process for the phosphorylation of the compound 1.

It is known that compound 2 is converted into compound 1 in the human body (DE 23 03 306, U.S. Pat. No. 4,254,129, U.S. Pat. No. 4,285,957, DE 30 07 498). It is furthermore known that ebastine is oxidized to carebastine with the aid of microorganisms, for example of the genus Cunninghamella (DE 40 34 218; Schwarz et al., *Appl. Microbiol. Biotechnol.* (1996)44: pages 731–735).

It has now been found that fungi of the genera Cunninghamella and Absidia convert the compound 2 selectively into the compounds of the formula I or II, set forth below. The selective oxidation only at the p-tertiary-butylphenyl radical of the compound 2 to give the corresponding carboxyl group is surprising, since the two hydroxyl groups in the compound 2 which could also be oxidized are not oxidized.

The present invention therefore relates to a process for obtaining the compound of the formula I

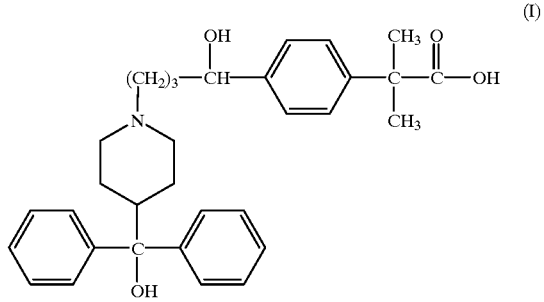

(I)

which comprises incubating α-(p-tert-butylphenyl)-4-(α-hydroxy-α-phenylbenzyl)-1-piperidinylbutanol with a fungus of the genus Cunninghamella or Absidia.

Preferably, the fungus is selected from *Cunninghamella blakesleeana, Cunninghamella elegans* or *Cunninghamella echinulata*. Most preferably, ATCC 8688a, DSM 1905, DSM 1908 or ATCC 9244 is employed as the fungus. Mutants and selectants of the fungi of the genus Cunninghamella are furthermore suitable for use in the process according to the present invention as long as they convert the compound 2 into a compound of the formula I and/or formula II set forth below. Fungi of the genus Cunninghamella can furthermore be employed for the phosphorylation of the compound 1.

A nutrient solution is employed in the process according to the present invention. The nutrient solution contains carbon sources such as sucrose, corn starch, dextrose or molasses and nitrogen sources such as soybean flour, groundnut flour, malt extract or ammonium acetate.

The nutrient medium also contains inorganic salts such as sodium hydrogenphosphate, sodium chloride, calcium chloride, calcium sulphate, calcium carbonate, magnesium sulphate or potassium hydrogen- phosphate. Furthermore, fat such as methyl oleate or soybean oil can be added to the nutrient medium. In addition, trace elements such as iron, manganese, copper, zinc, cobalt or other metal salts are also added.

The fungi are cultured at temperatures from 20° C. to 35° C., preferably at 28° C. and at pHs from 5 to 9, preferably at pH 8. Culturing is carried out aerobically, first in shaker flasks and then in a fermenter with stirring and aeration with air or pure oxygen. Culturing of the microorganisms in the fermenters is carried out over a time interval of 48 to 240 hours, preferably from 70 to 110 hours.

The addition of the compound 2 is carried out directly at the start of culturing but can also be carried out later, preferably after approximately 48 hours. The addition of the compound 2 is carried out as a solid substance, as a suspension or in solution.

Suitable solvents for the process according to the present invention include ethanol, dimethylformamide (DMF), dimethyl sulfoxide (DMSO), dimethylacetamide (DMA), dimethoxyethane (DME), tetrahydrofuran (THF), dibutyl-, diisopropyl- or diethylformamide, 1-methyl-, 1-ethyl- or 1-cyclohexylpyrrolidone, 4-formylmorpholine, 1-formylpiperidine, 1-formylpyrrolidine, tetramethyl-, tetraethyl- or tetrabutylurea, tripiperidino- or tripyrrolidino-phosphine oxide, sulfolane, N-methylcaprolactam or mixtures of the solvents mentioned. Preferably, the solvent is ethanol or dimethylformamide (DMF). Solubilizers such as ®Tween 80 or sodium dodecylsulfate can also be added.

The compound 1 is isolated directly from the nutrient solution or after separation of the cells, for example by centrifugation or filtration. The compound 1 can be isolated by extraction with solvents or by adsorption on hydrophobic resins or ion exchangers. Examples of these hydrophobic resins include polymeric adsorbents available from Rohm and Haas under the Tradename Amberlite, such as Amberlite XAD-16™ polyaromatic adsorbents and Amberlite XAD-16™ acrylic ester-based adsorbents, and HP-20, a hydrophobic polystyrol polymer available from Mitsubishi of Japan.

The present invention furthermore relates to a process for the preparation of the compound of the formula II

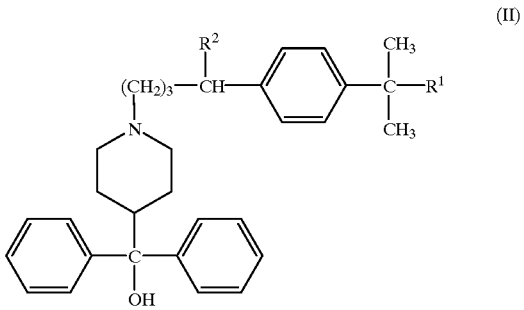

(II)

in which
$R^1$ is —OH or —$CH_2$—O—P(O)(OH)$_2$ and $R^2$ is —OH;
$R^1$ is —$CH_3$ and $R^2$ is —O—P(O)(OH)$_2$; or
$R^1$ is —C(O)OH and $R^2$ is —O—P(O)(OH)$_2$, comprising incubating α-(p-tert-butylphenyl)-4-(α-hydroxy-α-phenylbenzyl)-1-piperidinylbutanol or, if appropriate, 4-(4-(4-(hydroxydiphenyl)-1-piperidinyl)-1-hydroxybutyl)-α,α-dimethylphenylacetic acid with a fungus of the genus Cunninghamella or Absidia.

The reaction is carried out essentially as in the process for the preparation of the compound of the formula I. For the preparation of the compound of the formula II in which $R^1$ is —COOH and $R^2$ is —O—P(O)(OH)$_2$, compound 1 is preferably employed as a substrate for the reaction.

The present invention furthermore relates to novel compounds of the formula II, in which $R^1$ is —CH$_2$—O—P(O)(OH)$_2$ and $R^2$ is —OH (compound 3);

$R^1$ is —CH$_3$ and $R^2$ is —O—P(O)(OH)$_2$ (compound 4); or $R^1$ is —COOH and $R^2$ is —O—P(O)(OH)$_2$.

The present invention additionally relates to a process for the preparation of the compound of the formula II in which $R^1$ is —OH and $R^2$ is —OH (triol), which comprises incubating α-(p-tert-butylphenyl)-4-(α-hydroxy-α-phenylbenzyl)-1-piperidinylbutanol with a fungus of the genus Cunninghamella or Absidia.

The present invention also relates to pharmaceuticals comprising an efficacious amount of at least one compound of the formula II and/or of a physiologically tolerable salt of the compound of the formula II, together with a pharmaceutically suitable and physiologically tolerable excipient.

The present invention also includes pharmaceutically tolerable salts of the compound of the formula II. Pharmaceutically tolerable acid addition salts of compounds according to the present invention are those with suitable inorganic or organic acids. Suitable inorganic acids are, for example, hydrochloric acid, hydrobromic acid, sulfuric acid and phosphoric acid. Suitable organic acids include carboxylic acids such as acetic acid, propionic acid, glycolic acid, lactic acid, pyruvic acid, malonic acid, succinic acid, fumaric acid, malic acid, tartaric acid, citric acid, cyclamen acid, ascorbic acid, hydroxymaleic acid, dihydroxymaleic acid, benzoic acid, phenylacetic acid, 4-aminobenzoic acid, 4-hydroxybenzoic acid, anthranilic acid, cinnamic acid, salicylic acid, 4-aminosalicylic acid, 2-phenoxybenzoic acid, 2-acetoxybenzoic acid and mandelic acid, sulfonic acids such as methanesulfonic acid, ethanesulfonic acid and β-hydroxyethanesulfonic acid. Nontoxic salts of the compounds of the above formulae with inorganic or organic bases also come within the scope of the present invention. These include, for example, the salts with alkali metals such as sodium, potassium and lithium, with alkaline earth metals such as calcium and magnesium, light metals of group IIIA such as aluminum, with organic amines such as primary, secondary and tertiary amines, for example cyclohexylamine, ethylamine, pyridine, methylaminoethanol and piperazine. The salts are formed in a conventional manner, for example by reacting a compound of the formula II with the appropriate acid or base.

On account of the pharmacological properties, the compounds of the formula II according to the present invention are suitable as antihistamines, antiallergens and bronchodilators. The compounds of the formula II according to the present invention are suitable for the treatment of allergic rhinitis, asthma or other allergic disorders.

The compounds of the formula II according to the present invention can be administered orally, parenterally, for example, subcutaneously, intravenously, intramuscularly or intraperitoneally, by intranasal introduction or application to mucous membranes, for example, of the nose, of the throat or of the bronchial tract. Intranasal introduction or application to mucous membranes can be achieved using, for example, an aerosol spray which contains small particles of a compound according to the present invention in mist or powder form.

The amounts of the compounds to be administered depend on the patient and the manner of administration. The amount to be administered can vary within a wide range, such that dose units having an efficacious amount of approximately 0.01 to 20 mg/kg of body weight/day for achieving the desired effect result. For example, the desired antihistaminic, antiallergenic or bronchodilating action can be achieved by absorption of a dose unit such as, for example, a tablet having 5 to 300 mg of the compound according to the present invention, preferably 10 to 200 mg, which is taken 1 to 4 times daily.

The present invention also relates to a process for the production of a pharmaceutical composition, comprising bringing at least one compound of the formula II into a suitable administration form with a pharmaceutically suitable and physiologically tolerable carrier and, if appropriate, further suitable active compounds, additives or auxiliaries.

Suitable solid or pharmaceutical preparation forms are, for example, granules, powders, coated tablets, tablets, (micro)capsules, suppositories, syrups, juices, suspensions, emulsions, drops or injectable solutions and also preparations with protracted release of active compound. Those preparation forms further contain customary auxiliaries, such as excipients, disintegrants, binders, coating agents, swelling agents, glidants or lubricants, flavorings, sweeteners and solubilizers. Frequently used auxiliaries which may be mentioned are magnesium carbonate, titanium dioxide, lactose, mannitol and other sugars, talc, lactoprotein, gelatin, starch, cellulose and its derivatives, animal and vegetable oils such as cod liver oil, sunflower oil, groundnut or sesame oil, polyethylene glycol and solvents such as, for example, sterile water and mono- or polyhydric alcohols such as glycerol.

The compounds of the formula II according to the present invention can also be administered as injectable solutions or suspensions in a physiologically tolerable diluent with a pharmaceutical carrier which is a sterile liquid such as water or an oil, it being possible to add surface-active and other pharmaceutically permissible auxiliaries. Examples of suitable oils are those of petroleum, animal, vegetable or synthetic origin such as groundnut oil, soybean or mineral oil. In general, water, saline solution, aqueous dextrose solution or similar sugar solutions and glycols such as propylene glycol or polyethylene glycol are preferred as liquid carriers, in particular for injectable solutions.

For use as aerosols, the compounds according to the present invention are put under pressure in solution or suspension into an aerosol container together with suitable propellants, for example hydrocarbon propellants such as propane, butane or isobutane, or carbon dioxide or nitrogen or other ecologically permissible propellants and customary auxiliaries. The compounds can also be administered in unpressurized form, for example, using atomizers.

For administration, possible animals are warm-blooded animals, birds, and mammals, for example, humans, cats, dogs, horses, sheep, cattle, cows, pigs, lambs, rats, mice and guinea-pigs.

The following examples are illustrative of the invention embodied herein without being limiting in nature.

EXAMPLE 1

Maintenance of the Strain

100 µl of a spore suspension of the Cunninghamella strains *Cunninghamella blakesleeana* FH 001, *Cunninghamella blakesleeana* FH 002, *Cunninghamella blakesleeana* FH 003, *Cunninghamella echinulata* DSM 1905, *Cunninghamella echinulata* variant *elegans* ATCC 8688a, *Cunninghamella elegans* DSM 1908 and *Cunninghamella echinulata* variant *echinulata* ATCC 9244 are plated out on an agar plate (20 g/l of malt extract, 2 g/l of peptone and 20 g/l of agar pH 6.5) and incubated at 28° C. for 72 h. The plate can then be stored at 4° C. for at least eight weeks. Alternatively, the strains can be subjected to submerse culture in the same medium without addition of agar. After culturing for 72 h at 28° C., the culture is treated with 20% glycerol and the suspension is stored at approximately −120° C. over liquid nitrogen.

EXAMPLE 2

High-Pressure Liquid Chromatography (HPLC) Analysis

| Sample preparation: | Dilute culture broth 1:1 with methanol and stir suspension for 30 minutes. Separation of the clear phase by centrifugation. |
|---|---|
| Eluant A: | 900 ml of $H_2O$ |
| | 100 ml of acetonitrile |
| | 1 ml of trifluoroacetic acid (TFA) |
| Eluant B: | 900 ml of acetonitrile |
| | 100 ml of $H_2O$ |
| | 1 ml of TFA |
| Detection: | 215 nm |
| Flow rate: | 1 ml/min |
| Gradient: | 0 min  50% B |
| | 10 min  80% B |
| | 15 min  80% B |
| | 16 min  50% B |
| | 21 min  50% B |
| Column temperature: | 55° C. |
| Column: | Merck RP 18 5 μm Licrospher 100 |
| | Length 25 cm Diameter 4 mm |
| Retention times: | Compound 1  5.4 minutes (min) |
| | Compound 2  9 min |
| | Triol  5.7 min |
| | Compound 3  3.5 min |
| | Compound 4  6.9 min |

EXAMPLE 3

Screening with Cunninghamella Strains 100 ml of screening medium (5 gl of soybean peptone, 5 g/l of yeast extract, 5 g/l of NaCl, 5 g/l of $K_2HPO_4$, 3 g/l of agar and 20 g/l of glucose/separately autoclaved, pH 5.0 in an Erlenmeyer flask of 1000 ml volume) were inoculated with a piece of agar of one of the strains mentioned in Example 1. Culturing was first carried out for 48 h at 28° C. and 180 revolutions per minute (rpm) on a rotating shaker. After this time, the addition of 20 mg of the compound 2 dissolved in 100 μl of DMF or ethanol was carried out. After 72 hours (h), or alternatively an earlier time, an aliquot of the culture was taken and treated with 50% methanol. The suspension obtained was suspended with an Ultra-Turrax for 30 seconds and the suspension was then centrifuged at 10,000 g. The clear supernatant obtained was then analyzed by means of HPLC (see Example 2).

It was possible to detect the compound 1 in a concentration of up to 5 mg/l in the culture broth of all strains after an incubation time of 72 h.

EXAMPLE 4

Production of the Compound 1 on the Flask Scale using Various Cunninghamella Strains 100 ml of preculture medium (5 g/l of soybean peptone, 5 g/l of yeast extract, 5 g/l of NaCl, 5 g/l of $K_2HPO_4$, 3 g/l of agar and 20 g/l of glucose/separately autoclaved, pH 5.0 in an Erlenmeyer flask of 1000 ml volume) were inoculated with a piece of agar on which one of the strains mentioned in Example 1 had been grown in each case. Culturing was carried out for 48 h at 28° C. and 180 rpm on a rotating shaker. 100 ml of production medium (5 g/l of soybean peptone, 10 g/l of corn steep liquor, 20 g/l of glucose, 5 g/l of NaCl, 1 g/l of $K_2HPO_4$, 3 g/l of agar, 25.1 g/l of 2-([hydroxy-1,1-bis-(hydroxymethyl)ethyl]amino) ethanesulfonic acid (TES) (sodium salt), 100 μl of Desmophen, pH 8.0 in an Erlenmeyer flask of 500 ml volume) were inoculated with 10 ml of the preculture described above. Culturing was first carried out for 48 h at 28° C. and 180 rpm on a rotating shaker.

After this time, 20 mg of compound 2 dissolved in 100 μl of DMF were added. After 72 h an aliquot of the culture was taken and treated with 50% methanol. The suspension obtained was suspended for 30 seconds using an Ultra-Turrax and the suspension was then centrifuged at 10,000 g. The clear supernatant obtained was then analyzed by means of HPLC (Example 2).

The analysis gives the yields compiled in Table 1; the following compounds were found:

compound 1 is the compound of the formula I;

compound 2 is the compound of the formula II, in which $R^1$ is —$CH_3$ and $R^2$ is —OH;

compound 3 is the compound of the formula II, in which $R^1$ is —$CH_2$—O—P(O)(OH)$_2$ and $R^2$ is —OH;

compound 4 is the compound of the formula II, in which $R^1$ is —$CH_3$ and $R^2$ is —O—P(O)(OH)$_2$ and triol is the compound of the formula II, in which $R^1$ is —OH and $R^2$ is —OH.

TABLE 1

| Strain | Triol [mg/l] | Compound 1 [mg/l] | Compound 3 [mg/l] | Compound 4 [mg/l] |
|---|---|---|---|---|
| C. blak. FH 001 | 4.9 | <1.0 | 11.9 | 60.4 |
| C. blak. FH 002 | 26.0 | 50.7 | 42.5 | 3.0 |
| C. blak. FH 003 | 2.1 | <1.0 | 1.6 | 18.4 |
| C. echinu. ATCC 8688a | 4.7 | 43.2 | 27.3 | 2.2 |
| C. echinu. DSM 1905 | 13.8 | 3.3 | 40.4 | 23.1 |
| C. el. DSM 1908 | 17.3 | 1.1 | 15.2 | 37.0 |
| C. ech. ATCC 9244 | 18.5 | 5.1 | 20.7 | 7.4 |

EXAMPLE 5

Improved Preparation of the Compound 1 on the Flask Scale with *Cunninghamella echinulata* variant *elegans* ATCC 8688a 100 ml of preculture medium (5 g/l of soybean peptone, 5 g/l of yeast extract, 5 g/l of NaCl, 5 g/l of $K_2HPO_4$, 3 g/l of agar and 20 g/l of glucose (separately autoclaved), pH 5.0 in an Erlenmeyer flask of 1000 ml volume) were inoculated with a piece of agar on which one of the strains mentioned in Example 1 had been grown in each case. Culturing was carried out for 48 h at 28° C. and 180 rpm on a rotating shaker. 100 ml of production medium (5 g/l of soybean peptone, 5 g/l of casein peptone, 20 g/l of soluble starch, 5 g/l of NaCl, 1 g/l of $K_2HPO_4$, 1 g/l of $NH_4(SO_4)_2$, 3 g/l of agar, 25.1 g/l of TES (sodium salt), 100 μl of Desmophen, pH 8.0 (in an Erlenmeyer flask of 500 ml volume) were inoculated with 10 ml of the preculture described above. Culturing was first carried out for 24 h at 28° C. and 180 rpm on a rotating shaker.

After this time, 20 mg of compound 2 dissolved in 800 μl of ethanol were added. After 72 h an aliquot of the culture was taken and treated with 50% methanol. The suspension obtained was suspended for 30 seconds using an Ultra-Turrax and the suspension was then centrifuged at 10,000 g. The clear supernatant obtained was then analyzed by means of HPLC (Example 2). Analysis gave a yield of 145 mg/l of compound 1, 6.5 mg/l of triol (2), 22 mg/l of compound 3 and 5 mg/l of compound 4.

EXAMPLE 6

Production of Compounds of the Formula II in a 10 l Fermenter 100 ml of preculture medium (5 g/l of soybean peptone, 5 g/l of yeast extract, 5 g/l of NaCl, 5 g/l of $K_2HPO_4$, 3 g/l of agar and 20 g/l of glucose/separately autoclaved, pH 5.0 in an Erlenmeyer flask of 1000 ml volume) were inoculated with a piece of agar of the strain *Cunninghamella echinulata* var. *elegans* ATCC 8688a. Culturing was carried out for 48 h at 28° C. and 180 rpm on a rotating shaker. 10 l of production medium (5 g/l of soybean peptone, 5 g/l of yeast extract, 20 g/l of glucose (separately autoclaved), 5 g/l of NaCl, 1 g/l of $K_2HPO_4$, 100 µl of Desmophen, pH 5.0) were inoculated with 100 ml of the preculture described above. Compound 2 was then added such that a final concentration of 200 mg/l of production medium was achieved in the fermenter. Fermentation was carried out at 28° C., 700 rpm and 0.5 vvm for 96 hours.

According to HPLC analysis, the culture broth contained approximately 10 mg/l of compound 1, 10 mg/l of triol (2), 100 mg/l of compound 3 and 100 mg/l of compound 4.

EXAMPLE 7

Isolation of the Compounds of the Formula II

The culture broth obtained according to Example 6 (8800 ml) was separated into supernatant (8000 ml) and biomass (800 g) by means of a bucket centrifuge (5000 g/10 minutes) and both phases were worked up separately.

160 g of macroporous acrylamide/polystyrene adsorber resin such as XAD 7 were added to the supernatant. Adsorption was carried out with gentle stirring at pH 2.5 and room temperature for 2 hours. The adsorber resin was filtered off and eluted with 4 times 160 ml of methanol. The eluates were combined and concentrated to dryness under reduced pressure (approximately 50 g of oily solid after lyophilization). Fine purification was carried out by means of preparative HPLC according to the following procedure:

| | | |
|---|---|---|
| Eluant A: | 800 ml of $H_2O$ | |
| | 200 ml of acetonitrile | |
| | 1 ml of TFA | |
| Eluant B: | 1000 ml of acetonitrile | |
| | 0.9 ml of TFA | |
| Detection: | 215 nm | |
| Flow rate: | 50 ml/min | |
| Gradient: | 0 min | 0% B |
| | 60 min | 0% B |
| | 133 min | 43% B |
| | 134 min | 100% B |
| | 157 min | 100% B |
| Column temperature: | Room temperature | |
| Column: | Kromasil, C18, 7 µm | |
| | Length 350 mm, diameter 50 mm | |
| Sample | 5 g of crude product, dissolved in 350 ml of methanol/water (1:1) | |

After combination of the appropriate fractions, concentration under reduced pressure and lyophilization of the aqueous residue, 20 mg of compound 1 and 160 mg of compound 3 were obtained from two runs.

The biomass (800 g) was extracted with n-propanol, 30% strength and 100% strength (total 1500 ml) and the solid is separated off by means of filtration through filter layers (K300). The filtrates were concentrated under reduced pressure and 26.2 g of oily solid were obtained.

Fine purification was carried out by means of preparative HPLC according to the following procedure:

| | | |
|---|---|---|
| Eluant A: | 800 ml of $H_2O$ | |
| | 200 ml of acetonitrile | |
| | 1 ml of TFA | |
| Eluant B: | 1000 ml of acetonitrile | |
| | 0.9 ml of TFA | |
| Detection: | 215 nm | |
| Flow rate: | 50 ml/min | |
| Gradient: | 0 min | 0% B |
| | 34 min | 0% B |
| | 121 min | 51% B |
| | 122 min | 100% B |
| | 148 min | 100% B |
| Column temperature: | Room temperature | |
| Column: | Kromasil, C18, 7 µm | |
| | Length 350 mm, diameter 50 mm | |
| Sample | 5 g of crude product, dissolved in 400 ml of methanol/water (1:1) | |

After combination of the appropriate fractions, concentration under reduced pressure and lyophilization of the aqueous residue, 4 mg of triol (2), 20 mg of compound 4 and 80 mg of compound 1 were obtained from two runs.

EXAMPLE 8

Characterization of the Compounds of the Formula II

In addition to characterization by means of UV/VIS spectroscopy, the components were characterized by $^1$H-NMR and ESI-MS or FAB-MS. MS data:

| | |
|---|---|
| Triol (2) | ESI-MS: m/e = 488.4 $[M + H]^+$ |
| Compound 1 | ESI-MS: m/e = 502.3 $[M + H]^+$ |
| Compound 3 | ESI-MS: m/e = 568.3 $[M + H]^+$ |
| | HR-FAB-MS: m/e = 568.2827 $[M + H]^+$ |
| Compound 4 | ESI-MS: m/e = 552.3 $[M + H]^+$ |

$^1$H-NMR data are shown in Table 2:
$^1$H chemical shifts in DMSO at 300° K.

TABLE 2

| | Compound 1 | Compound 3 | Triol 2 | Compound 4 |
|---|---|---|---|---|
| 1-$CH_3$ | 1.45 | 1.25 | 1.20 | 1.25 |
| 1-$CH_2$ | — | 3.83 | 3.39 | — |
| 3 | 7.30 | 7.34 | 7.30 | 7.32 |
| 4 | 7.28 | 7.26 | 7.23 | 7.27 |
| 6 | 4.52 | 4.52 | 4.51 | 5.11 |
| 7 | 1.66/1.59 | 1.68/1.59 | 1.68/1.58 | 1.71 |
| 8 | 1.59 | 1.58 | 1.58 | 1.73 |
| 9 | 2.98 | 2.98 | 2.97 | 2.97 |
| 10 | 3.43/2.89 | 3.43/2.89 | 3.41/2.88 | 3.31/2.83 |
| 11 | 1.66/1.46 | 1.66/1.45 | 1.66/1.46 | 1.74/1.37 |
| 12 | 2.83 | 2.83 | 2.82 | 2.81 |
| 15 | 7.49 | 7.49 | 7.49 | 7.50 |
| 16 | 7.28 | 7.29 | 7.30 | 7.28 |
| 17 | 7.16 | 7.16 | 7.16 | 7.15 |

EXAMPLE 9

Action on the Bronchial Diameter of the Anesthetized Guinea-Pig

The investigations were carried out according to the method of Konzett-Rössler (*Arch. exp. Path. U. Pharmak.* 195 (71–74) 1940), on male albino guinea-pigs having a body weight of 312–415 g. The test preparations were administered in a dose of 10 mg/kg in a suspension with the administration volume of 2 ml/kg of body weight. After two preliminary values with histamine 20 µg/kg intravenously (i.v.), the substance was administered a single time by means of a duodenal tube and the asthma testing was repeated 15, 30, 60, 90, 120, 150, 180, 210 and 240 min after administration of preparations.

The alterations of the bronchial diameter in comparison to the control measurements were given in percentages. 6 animals were employed per dose. Statistics were obtained by means of the t-test.

The results are shown in Table 3.

TABLE 3

| | Inhibition of the histamine-induced asthma attack in % | | | | | | | | |
|---|---|---|---|---|---|---|---|---|---|
| Preparation | 15 min | 30 min | 60 min | 90 min | 120 min | 150 min | 180 min | 210 min | 240 min |
| Terfenadine (TELDANE ®)* | 11.7 ± 9.4 | 26.8 ± 14.3 | 38.2 ± 13.9 | 61.8 ± 11.5 | 83.5 ± 12.5 | 88.0 ± 4.8 | 87.6 ± 6.6 | 81.2 ± 9.3 | 75.4 ± 11.2 |
| Compound 3 | 30.7 ± 21.7 | 66.2 ± 17.2 | 85.7 ± 8.9 | 84.3 ± 15.7 | 88.7 ± 6.3 | 91.8 ± 3.8 | 91.3 ± 3.8 | 94.0 ± 2.7 | 92.6 ± 4.9 |
| Compound 4 | 68.3 ± 16.7 | 91.8 ± 3.3 | 94.2 ± 2.0 | 93.5 ± 1.9 | 94.5 ± 1.5 | 93.8 ± 1.2 | 91.7 ± 1.7 | 93.7 ± 1.2 | 92.0 ± 3.6 |

Dose = 10 mg/kg intraduodenally
N = 6/dose
* = suspension; converted to active compound Table 3 shows that compound 3 achieved its maximal action most rapidly (60 min post-administration (p.a.)) and the action lasted almost undecreased for up to 240 min p.a., compound 4 showed a slower onset of action (approximately 150 min p.a.).

Terfenadine showed a maximum action after 150 min p.a. and the onset of action after 60 min. p.a. compounds 3 and 4 are more rapidly and highly active than terfenadine.

What is claimed:

1. A compound of the formula II

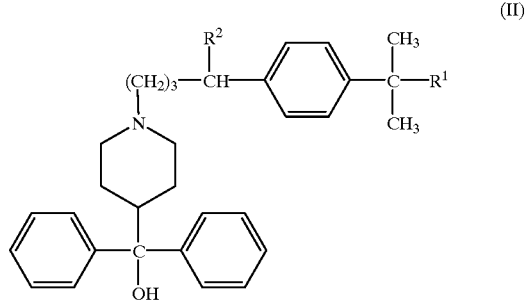

in which $R^1$ is —$CH_2$—O—$P(O)(OH)_2$ and $R^2$ is —OH;
$R^1$ is —$CH_3$ and $R^2$ is —O—$P(O)(OH)_2$; or
$R^1$ is —COOH and $R^2$ is —O—$P(O)(OH)_2$.

2. A process for the preparation of the compound of the formula II

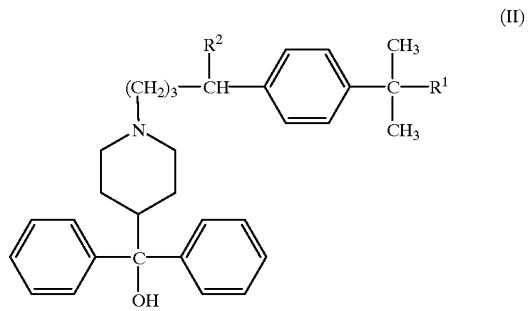

in which $R^1$ is —OH or —$CH_2$—O—$P(O)(OH)_2$ and $R^2$ is —OH;
$R^1$ is —$CH_3$ and $R^2$ is —O—$P(O)(OH)_2$; or
$R^1$ is —COOH and $R^2$ is —O—$P(O)(OH)_2$,
comprising incubating α-(p-tertiary-butylphenyl)-4-(α-hydroxy-α-phenylbenzyl)-1-piperidinylbutanol or 4-(4-(4-hydroxydiphenyl)-1-piperidinyl)-1-hydroxybutyl)-α,α-dimethylphenylacetic acid with a fungus of the genus Cunninghamella or Absidia.

3. A pharmaceutical composition comprising an effective amount of at least one compound of the formula II according to claim 1 in combination with a pharmaceutically suitable and physiologically tolerable excipient.

4. A method for the treatment of allergic disorders, allergic rhinitis or asthma, comprising administering to a patient in need of said treatment an effective amount of a pharmaceutical composition comprising at least one compound of the formula II according to claim 1 and a pharmaceutically suitable and physiologically tolerable excipient.

5. A process for the production of the pharmaceutical according to claim 3, comprising processing at least one compound of the formula II according to claim 1 and a pharmaceutically suitable and physiologically tolerable excipient to produce a suitable administration form.

6. A process for obtaining the compound of the formula I

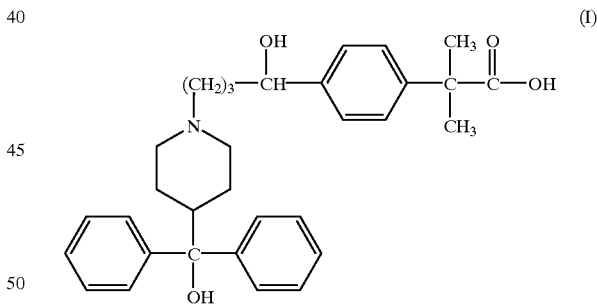

comprising incubating α-(p-tert-butylphenyl)-4-(α-hydroxy-α-phenylbenzyl)-1-piperidinylbutanol with a fungus of the genus Cunninghamella or Absidia.

7. A process according to claim 6, wherein the fungus is *Cunninghamella blakesleeana, Cunninghamella elegans* or *Cunninghamella echinulata*.

8. A process according to claim 7, wherein the fungus is *Cunninghamella echinulata* variant *elegans* ATCC 8688a, *Cunninghamella echinulata* DSM 1905, *Cunninghamella elegans* DSM 1908 or *Cunninghamella echinulata* ATCC 9244.

9. The process according to claim 2, wherein α-(p-tert-butylphenyl)-4-(α-hydroxy-α-phenylbenzyl)-1-piperidinylbutanol is added at the start of the culturing of the fungus of the genus Cunninghamella.

10. The process according to claim 2, wherein α-(p-tert-butylphenyl)-4-(α-hydroxy-α-phenylbenzyl)-1-piperidinylbutanol is added 24 hours after the start of the culturing of the fungus of the genus Cunninghamella.

11. The process according to claim 6, wherein α-(p-tert-butylphenyl)-4-(α-hydroxy-α-phenylbenzyl)-1-piperidinylbutanol is added at the start of the culturing of the fungus of the genus Cunninghamella.

12. The process according to claim 6, wherein α-(p-tert-butylphenyl)-4-(α-hydroxy-α-phenylbenzyl)-1-piperidinylbutanol is added 24 hours after the start of the culturing of the fungus of the genus Cunninghamella.

13. The process according to claim 7, wherein α-(p-tert-butylphenyl)-4-(α-hydroxy-α-phenylbenzyl)-1-piperidinylbutanol is added at the start of the culturing of the fungus of the genus Cunninghamella.

14. The process according to claim 7, wherein α-(p-tert-butylphenyl)-4-(α-hydroxy-α-phenylbenzyl)-1-piperidinylbutanol is added 24 hours after the start of the culturing of the fungus of the genus Cunninghamella.

* * * * *